United States Patent
Ambrosi et al.

(10) Patent No.: US 6,466,739 B2
(45) Date of Patent: Oct. 15, 2002

(54) ELECTRIC EVAPORATOR FOR INSECTICIDES OR PERFUMES IN LIQUID FORMULATION, WITH ADJUSTABLE EVAPORATION INTENSITY

(75) Inventors: Stefano Ambrosi, Gardolo; Stefano Baldessari, Caldonazzo; Paolo Campedelli, Mori; Filippo Stenico, Trento, all of (IT)

(73) Assignee: Zobele Holding S.p.A., Trento (IT)

( * ) Notice: Subject to any disclaimer, the term of this patent is extended or adjusted under 35 U.S.C. 154(b) by 0 days.

(21) Appl. No.: 09/916,275

(22) Filed: Jul. 30, 2001

(65) Prior Publication Data

US 2002/0021892 A1 Feb. 21, 2002

(30) Foreign Application Priority Data

Jul. 28, 2000 (IT) .......................................... MI20A1751

(51) Int. Cl.$^7$ .................................................. F24F 6/08
(52) U.S. Cl. ...................................................... 392/395
(58) Field of Search .................................. 392/390, 392, 392/394, 395; 122/366; 261/142, 99, DIG. 65

(56) References Cited

U.S. PATENT DOCUMENTS 4,621,768 A * 11/1986 Lhoste et al. .................. 239/44
4,663,315 A * 5/1987 Hasegawa et al. ............. 239/44
5,038,394 A * 8/1991 Hasegawa et al. .......... 392/392
5,095,647 A * 3/1992 Zobele et al. ................ 239/135
5,222,186 A * 6/1993 Schimanski et al. ........ 392/392
6,145,241 A * 11/2000 Okuno ......................... 222/187
6,285,830 B1 * 9/2001 Basaganas Millan   261/DIG. 65

FOREIGN PATENT DOCUMENTS

| EP | 0 943 344 A1 | 9/1999 |
| WO | 98/19526 | 5/1998 |
| WO | 98/58692 | 12/1998 |

* cited by examiner

*Primary Examiner*—Sang Paik
(74) *Attorney, Agent, or Firm*—Young & Thompson

(57) ABSTRACT

An electric evaporator for insecticides or perfumes in liquid formulation, contained in a bottle which can be steadily inserted into a container, includes a wick, an element for housing and centering the wick and a respective electric heating device. The wick housing and centering element are joined to the walls of the container through elastic bridge-pieces which have the shape of a loop extending respectively in horizontal and vertical planes. A cam device, which is actuated manually outside of the container, allows displacement of the wick housing and centering element in a direction perpendicular to the axis of the wick, towards or away from the heating device.

9 Claims, 2 Drawing Sheets

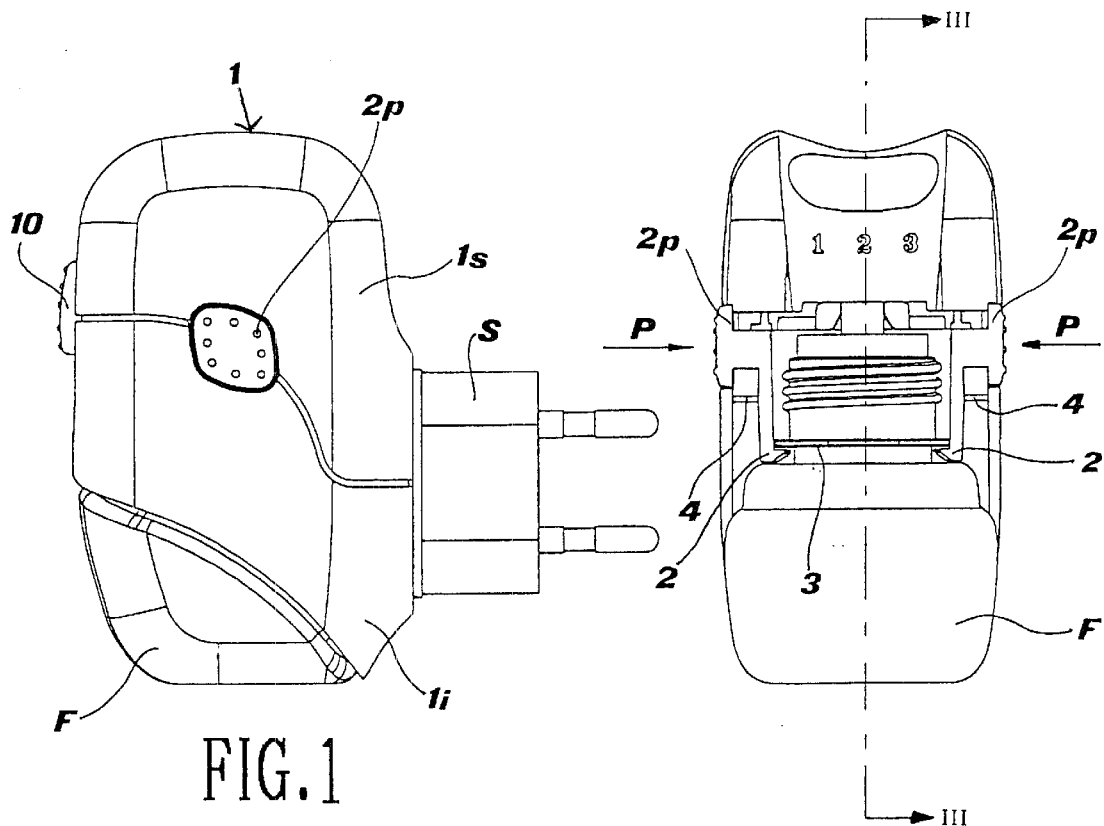
FIG.1
FIG.2
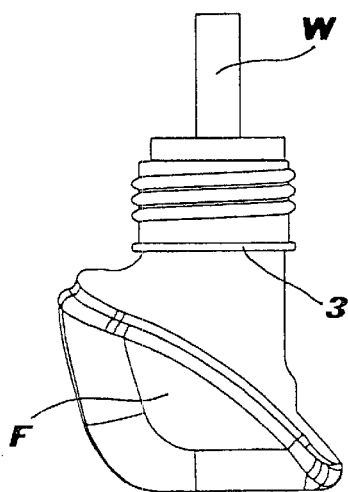
FIG.3

ELECTRIC EVAPORATOR FOR INSECTICIDES OR PERFUMES IN LIQUID FORMULATION, WITH ADJUSTABLE EVAPORATION INTENSITY

BACKGROUND OF THE INVENTION

The present invention relates to an electric evaporator for insecticides or perfumes, the intensity of which can be adjusted, and in particular to a evaporator for liquid formulations in which the flow of active substance emitted may be continuously regulated between a minimum and a maximum level.

In the field of electric home evaporators used with liquid formulations, evaporators are already known wherein the intensity of evaporation of the active substance may be adjusted by modifying the relative position of the heating device—which is normally an electric resistance or a PTC—with respect to that of the wick dipping in the bottle containing the liquid solution of active substance.

These known devices may be divided into different categories which will be briefly examined below, with reference also to the main drawbacks associated therewith.

In a first category of evaporators, the heating device can be moved towards or away from the wick in the bottle containing the active liquid solution, by means of a mechanical device, for example of the screw/nut thread type, so that the heat flow striking the wick itself may be increased or decreased. A device of this type is for disclosed in E-U-8800978. The drawbacks of this type of device are associated with the high manufacturing cost—owing to the large number of component parts and the consequent expensive nature of the assembly operations which must be performed, at least partially, by hand—and also the safety and duration of the electrical connections between the plug and the heating device, which connections are subject to continuous movement during the evaporator adjustment operations. Moreover, the adjustment of the evaporation intensity is fairly approximate, both as regards the constancy of minimum and maximum levels and above all as regards the repeatability and the linear variation of the intermediate levels. In fact, the movements of the heating device often result in an irregular alteration in the distribution of the heat flow, due to the presence of the various parts of the evaporator which create obstacles to said flow.

In a second category of evaporators, the heating device is fixed and the bottle is displaced along its axis, by a mechanical device, for example of the screw/nut thread type or simply a friction device, so as to increase or reduce the overlapping zone between wick and heating device. A device of this type is for example disclosed in EP-A-0942648 and in it the problems of safety and duration of the electrical connections are overcome. In the case of devices which use a screw/nut thread mechanism there remains the drawback—already seen for the devices in the first category—of the high manufacturing cost, while in the case of devices of the friction type, which have a simpler and more inexpensive design, the main drawback consists in the lack of maneuverability and the instability of the desired adjustment position.

In a third and last category of evaporators, the heating device is fixed to the plug and rotates with it, as disclosed in EP-A-0943344. The body of the plug comprises a screw/nut thread or cam system, so that it allows the axial or lateral displacement of the body itself and consequently of the heating device with respect to the wick, in the various possible positions assumed by the plug. In these devices also the problem of the electrical connections is satisfactorily dealt with, in that the connections are obviously not subject to any movement during rotation of the plug. It remains however the problem of a manufacturing cost which is still too high—although it is lower then that of the devices in the preceding categories—due to the fact that a specially designed plug, and not a standard rotatable plug, is used. Moreover, the evaporation adjustment system allows only two-position adjustment, i.e. either a minimum flow or a maximum flow, and therefore it is not possible to adjust with continuity and precision the evaporation flow between a minimum level and a maximum level.

SUMMARY OF THE INVENTION

The object of the present invention is therefore to provide an electric evaporator for insecticides or perfumes, of the type for use with liquid formulations, in which it is possible to obtain an optimum and continuous adjustment in the flow of evaporated active substance between a minimum level and a maximum level, without the need for use of complex mechanisms of the screw/nut thread type and also avoiding any displacement of the electrical connections of the heating device during the evaporation-flow adjustment operations.

Another object of the present invention is to provide a evaporator for insecticides or perfumes, in which the bottle containing the liquid active substance may be fixed inside the heating unit in an easy, quick and safe manner; in particular said bottle must offer a high level of safety with regard to accidental removal of the bottle by young children.

These objects are achieved, according to the present invention, by means of an electric evaporator for insecticides or perfumes in liquid formulation, contained in a bottle provided with a wick, of the type in which said bottle can be steadily inserted into a container, the inside of said container being further provided with an element for housing and centering said wick and with a respective electric heating device, characterized in that said wick housing and centering element is fixed to the walls of the container through elastic means which allow displacements of said element in a direction perpendicular to the axis of the wick towards or away from said heating device and in that a cam device which can be actuated manually outside of said container is further provided for effecting said displacements of the wick housing and centering element.

BRIEF DESCRIPTION OF THE DRAWINGS

Further characteristic features and advantages of the present invention will emerge, however, more clearly from the following detailed description of a preferred embodiment thereof, provided with reference to the accompanying drawings, in which:

FIG. 1 is a side elevation view of the evaporator according to the present invention, provided with the bottle containing the liquid formulation;

FIG. 2 is a rear view of the evaporator according to FIG. 1, with part of the bottom shell of the evaporator and the actuating pushbutton removed, so as to show the arrangement of the bottle and the relative locking system;

FIG. 3 is a side elevation view of the only bottle used in the evaporator according to FIG. 1;

DESCRIPTION OF THE PREFERRED EMBODIMENTS

Figure 6:
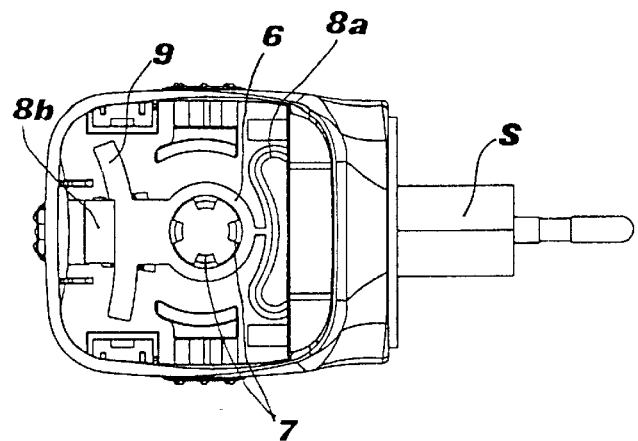
FIG. 6 is a bottom plan view of the evaporator according to FIG. 1, showing the evaporation adjustment system.

As it can clearly be seen in the various views which are shown in the drawings, the evaporator according to the present invention consists of an external container 1 formed in a conventional manner by a top shell 1s and a bottom shell 1i which are snap-engaged together. A rotating plug S is located between the two shells 1s and 1i, said plug also being of the type widely known in the sector and suitable for supplying electrical power to a heating device which is steadily housed inside the top shell 1s.

The bottom shell 1i is completely devoid of a bottom wall so as to allow insertion therein of the bottle F. The latter, once it has been inserted into the shell 1i and has been fastened thereto, forms an integral part of the evaporator and also forms the support base, when the evaporator is not inserted into an electrical socket, but is placed on a surface. In order to obtain stable fastening and firm locking of the bottle F inside the shell 1i, according to the invention a pair of opposite hook elements 2 are envisaged, said hook elements being snap-fastened underneath a thin annular rib 3 formed on the neck of the bottle F when the bottle itself is pushed into position inside the shell 1i.

The hook elements 2 have a certain extension heightwise and terminate, on the opposite side to the hook-shaped end, in an end widened in the form of a pushbutton 2p which protrudes from the container 1 along the line of separation between the two shells 1s and 1i. The hook elements 2 are formed integrally with the shell 1i to which they remain attached by thin bridge-pieces 4 along a central zone of the hook elements 2, so that the hook elements are able to pivot about said bridge-pieces—making use of their flexibility—between the engaged position, shown in FIG. 2, and a splayed position where the hook elements 2 free the rib 3, thereby allowing the bottle F to be extracted from the shell 1i. In view of the impossibility of any lateral displacement of the bottle F, which is precisely fitted inside the bottom shell 1i, extraction of the bottle may therefore take place only if the two pushbuttons 2p are pressed simultaneously in the direction of the arrows P, thus ensuring a reliable safety system, preventing accidental extraction of the bottle F by young children.

Figure 4:
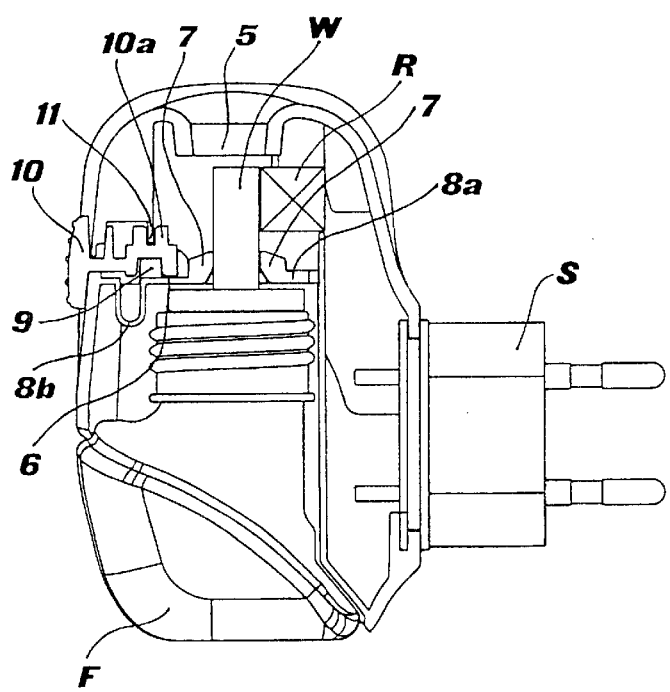
FIG. 4 is a cross-sectional view, along the line III—III of FIG. 2.

The top shell is, as can be clearly seen in the cross-section in FIG. 4, has in its top wall a central flue hole 5 from which the vapours of the active substance emitted by the underlying wick W of the bottle F emerge. The hole 5 has a diameter which is greater than that of the wick W so as to be able to embrace the various possible positions which the wick W may assume, as will become clear from the description which follows.

According to a main characteristic feature of the present invention, the wick W of the bottle F is housed and centered inside the evaporator 1 by means of an annular support 6 which has, projecting therefrom, several fingers 7 which come into contact with the lateral surface of the wick W, defining the position thereof. The annular support 6 is formed integrally with the bottom shell 1i and is joined thereto by means of bridge-pieces 8a and 8b of plastic material. Said bridge-pieces have a configuration such as to provide them with a shape elasticity sufficient to allow small displacements of the annular support 6 and, together therewith, of the wick W, in a direction perpendicular to the axis of the wick, during movement thereof towards or away from the heating device R.

Figure 5:
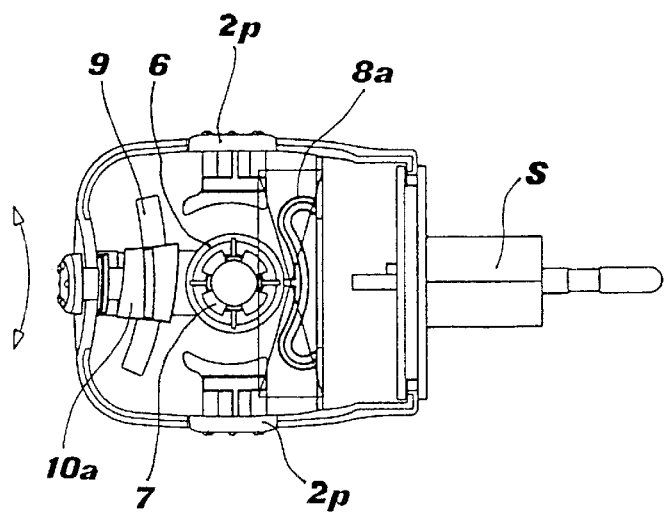
FIG. 5 is a top plan view of the evaporator according to FIG. 1, with the top shell removed, so that evaporation adjustment system is visible.

More particularly, the bridge-pieces 8a and 8b have different shapes so as to ensure that the possibility of displacement of the annular support 6 in the desired direction may be accompanied by excellent stability thereof as regards unwanted displacements in the other two possible directions. In particular, the bridge-piece 8a has the shape of a loop in a horizontal plane, as can be seen in FIGS. 5 and 6, which prevents however displacements of the support 6 in a vertical direction, while the bridge-piece 8b has the shape of a loop in a vertical plane, so as to prevent displacements of the support 6 in the other direction perpendicular to the axis of the wick, i.e. the one parallel to the longitudinal axis of the heating device R.

The desired displacements of the annular support 6 may be effected by the user with the aid of a cam device. This device consists of a cam profile 9, in the form of an arc with variable radius, formed integrally with the annular support 6, and a cam-following cursor 10, which is formed as a single piece separate from the shells 1a and 1b and has an outer operating pushbutton and an inner end 10a intended to co-operate with the cam profile 9. Said inner end 10a has in fact a pair of opposite grooves, one of which is guided by a profiled arc 11 with a constant radius, formed integrally with the top shell 1s, while the opposite groove determines the position of the cam profile 9, causing the movement of the support 6 and therefore of the wick W away from or towards the heating device R.

The evaporator having the above described structure according to the present invention, is obtained by means of a simple moulding process involving three elements: namely the two shells 1s and 1i, complete with all the necessary detailed parts for obtaining the desired adjustment of the flow, as well as the cursor 10 for actuating the cam device. The cost of manufacture of this evaporator is therefore much lower than that of known adjustable-flow evaporators and basically substantially the same as that of a evaporator without flow adjustment, thus fully achieving a first object of the invention.

By operating the sliding pushbutton of the cursor 10 it is therefore possible to adjust the position of the annular support 6, and thus of the wick W, in any desired position between the position closest to the heating device R, which is the maximum outflow position, and a minimum outflow position, which may obviously be varied during design, depending on the type of evaporator, by simply modifying the curvature of the variable-radius cam profile 9.

It should also be noted that operation of the cursor 10 is of the non-reversible type and therefore the associated pushbutton may be steadily arranged in any intermediate position—from which it does not move unless actuated again by the operator—thus allowing the user to perform continuous, stable and repeatable adjustment of the flow of active substance emitted, between said minimum and maximum levels, thereby achieving a second object of the invention.

Finally, the special system for fastening and locking the bottle is not only extremely simple and inexpensive, but also very safe vis-à-vis young children. Activation of the locking system is in fact performed by simply pressing the bottle F into its housing, since the annular rib 3 splays the hook elements 2, acting on their inclined external surface. Once fastening has been performed, release of the bottle is possible only by pressing simultaneously the two pushbuttons 2p in opposite directions, it being particularly difficult for said operation to be performed in a random manner by a child, thus achieving a third object of the invention.

The present invention has been described with reference to a preferred embodiment, but it is clear that the scope of protection of the invention is not limited thereto but is extended to include the numerous variations and modifications which are within the competence of a person skilled in the art who is acquainted with the present invention, provided that it falls within the scope of the accompanying claims. For example, the system for adjusting the position of the wick may, without significant modifications, be used to adjust instead the position of the heating device, keeping the wick steady, or the position of both these elements may be adjustable, where this is necessary or advantageous.

What is claimed is:

1. An electric evaporator for insecticides or perfumes in liquid formulation, contained in a bottle provided with a wick, of the type in which said bottle can be steadily inserted into a container, the inside of said container being further provided with an element for housing and centering said wick and with a respective electric heating device, characterized in that said wick housing and centering element is joined to the walls of the container through elastic means which allow displacements of said element in a direction perpendicular to the axis of the wick towards or away from said heating device and in that the cam device which can be actuated manually outside of said container is further provided for effecting said displacements of the wick housing and centering element.

2. The electric evaporator as in claim 1, wherein said wick housing and centering element are formed integrally with the container and are joined to said container by means of a plurality of connecting bridge-pieces which have a shape elasticity and constitute said elastic means.

3. The electric evaporator as in claim 2, wherein said bridge-pieces are two in number and are arranged on opposite sides of said element, in the direction of displacement of the wick housing and centering element.

4. The electric evaporator as in claim 3, wherein at least one of said bridge-pieces has the shape of a loop extending in a horizontal plane.

5. The electric evaporator as in claim 3, wherein at least one of said bridge-pieces has the shape of a loop extending in a vertical plane.

6. The electric evaporator as in claim 1, wherein said cam device consists of a cam profile in the form of an arc with a variable radius, integral with said wick housing and centering element, and a cam-following cursor, which is actuated on the outside of the container and an operating end of the cursor is engaged on one side with said cam profile and on the other side with a profiled arc with a constant radius, integral with said container.

7. The electric evaporator as in claim 1, wherein said container is formed by top and bottom shells which are obtained by means of injection-moulding of a suitable plastic material and are snap-engaged together, the top shell having on a top wall a venting hole for the active substance vapours and the bottom shell having on a bottom wall a large opening for insertion of said bottle.

8. The electric evaporator as in claim 7, wherein said bottom shell also comprises means for snap-fastening of said bottle.

9. The electric evaporator as in claim 8, wherein said snap-fastening means consist of a pair of opposite hook elements having one end in the form of a pushbutton protruding from said container, said hook elements being formed integrally with the container and joined thereto, in a central position, by at least one flexible connecting bridge-piece.

* * * * *